(12) United States Patent
Mansour (10) Patent No.: US 9,370,447 B2
(45) Date of Patent: Jun. 21, 2016

(54) PROBES FOR USE IN OPHTHALMIC AND VITREORETINAL SURGERY

(75) Inventor: Fouad Mansour, Sandy Springs, GA (US)

(73) Assignee: CYGNUS LP, Roswell, GA (US)

( * ) Notice: Subject to any disclaimer, the term of this patent is extended or adjusted under 35 U.S.C. 154(b) by 0 days.

(21) Appl. No.: 13/270,028

(22) Filed: Oct. 10, 2011

(65) Prior Publication Data

US 2013/0090635 A1 Apr. 11, 2013

(51) Int. Cl.
*A61F 9/007* (2006.01)
*A61F 9/008* (2006.01)
*A61B 18/18* (2006.01)
*A61F 9/009* (2006.01)

(52) U.S. Cl.
CPC ............ *A61F 9/00821* (2013.01); *A61F 9/009* (2013.01); *A61F 2009/00863* (2013.01); *A61F 2009/00874* (2013.01)

(58) Field of Classification Search
None
See application file for complete search history.

(56) References Cited

U.S. PATENT DOCUMENTS

| | | | | |
|---|---|---|---|---|
| 4,405,314 A | * | 9/1983 | Cope | 604/510 |
| 5,123,902 A | * | 6/1992 | Muller et al. | 604/21 |
| 5,156,604 A | * | 10/1992 | Hessel et al. | 606/15 |
| 5,217,465 A | * | 6/1993 | Steppe | 606/107 |
| 5,231,989 A | * | 8/1993 | Middleman et al. | 600/434 |
| 5,275,593 A | * | 1/1994 | Easley et al. | 606/4 |
| 5,281,214 A | * | 1/1994 | Wilkins et al. | 606/15 |
| 5,300,061 A | * | 4/1994 | Easley et al. | 606/2 |
| 5,323,766 A | * | 6/1994 | Uram | 600/108 |
| 5,364,340 A | * | 11/1994 | Coll | 604/8 |
| 5,372,585 A | * | 12/1994 | Tiefenbrun et al. | 604/59 |
| 5,409,457 A | * | 4/1995 | del Cerro et al. | 604/521 |
| 5,447,512 A | * | 9/1995 | Wilson et al. | 606/139 |
| 5,512,034 A | * | 4/1996 | Finn et al. | 600/138 |
| 5,520,222 A | * | 5/1996 | Chikama | 138/118 |
| 5,603,710 A | * | 2/1997 | Easley et al. | 606/15 |
| 5,656,011 A | * | 8/1997 | Uihlein et al. | 600/146 |
| 5,741,225 A | * | 4/1998 | Lax et al. | 604/22 |

(Continued)

FOREIGN PATENT DOCUMENTS

| | | | | |
|---|---|---|---|---|
| EP | | 682910 A1 * | 11/1995 | A61B 1/00 |
| WO | WO | 9824513 A1 * | 6/1998 | A61N 5/06 |

OTHER PUBLICATIONS

Thierry et al., Blood Compatibility of Nitinol Compared to Stainless Steel, Proceedings of the International Conference on Shape Memory and Superelastic Technologies, SMTS-2000, 2000.*

(Continued)

*Primary Examiner* — Lynsey Crandall
*Assistant Examiner* — Manolis Pahakis (57) ABSTRACT

A probe for endo-ocular photocoagulation procedures provides straight and curved tip configurations. A flexible tubular material, pre-formed with a radius of curvature, allows the tip to be inserted through a trocar cannula and to resume its pre-formed shape for use during a surgical procedure. Alternatively, a tubular material is pre-formed with a radius of curvature, and is stiffened by use of a preferably stainless steel tube. Inside the tubular material is a distal end of at least one optical fiber, inserted such that its tip is coterminous with the tubular material. A tube surrounds the optical fiber and is free to move along the axis of the assembly, acting to straighten the tubular and optical fiber members as it moves forward via a sliding member associated with the hand piece. Illumination energy, laser energy, or both may be supplied to the targeted surgical site.

22 Claims, 5 Drawing Sheets

(56) References Cited

U.S. PATENT DOCUMENTS

| | | | |
|---|---|---|---|
| 5,825,958 A * | 10/1998 | Gollihar et al. | 385/125 |
| 5,891,022 A * | 4/1999 | Pologe | 600/323 |
| 6,015,403 A * | 1/2000 | Jones | 606/4 |
| 6,197,003 B1 * | 3/2001 | Howard et al. | 604/164.12 |
| 6,254,568 B1 * | 7/2001 | Ponzi | 604/95.04 |
| 6,572,608 B1 | 6/2003 | Lee et al. | |
| 6,575,989 B1 * | 6/2003 | Scheller et al. | 606/161 |
| 6,616,628 B2 * | 9/2003 | Hayzelden | 604/95.04 |
| 6,984,230 B2 | 1/2006 | Scheller et al. | |
| 7,066,942 B2 * | 6/2006 | Treace | 606/92 |
| 7,141,048 B1 * | 11/2006 | Charles | 606/4 |
| 7,267,674 B2 | 9/2007 | Brucker et al. | |
| 7,402,158 B2 | 7/2008 | Scheller et al. | |
| 7,473,249 B2 | 1/2009 | Scheller et al. | |
| 7,618,177 B2 * | 11/2009 | Cazzini | A61B 1/00165 362/551 |
| 7,766,904 B2 * | 8/2010 | Mc Gowan et al. | 606/13 |
| 7,909,816 B2 | 3/2011 | Buzawa | |
| 7,922,645 B2 * | 4/2011 | Kaplan | 600/3 |
| 8,317,778 B2 * | 11/2012 | Spaide | 606/4 |
| 2003/0088257 A1 * | 5/2003 | Awh et al. | 606/161 |
| 2005/0154379 A1 * | 7/2005 | McGowan et al. | 606/4 |
| 2006/0004348 A1 * | 1/2006 | Scheller et al. | 606/4 |
| 2006/0149194 A1 * | 7/2006 | Conston et al. | 604/294 |
| 2006/0173448 A1 * | 8/2006 | Scheller et al. | 606/15 |
| 2007/0265602 A1 * | 11/2007 | Mordaunt et al. | 606/4 |
| 2008/0188910 A1 * | 8/2008 | Spaide | 607/89 |
| 2008/0262442 A1 * | 10/2008 | Carlin et al. | 604/264 |
| 2009/0093800 A1 * | 4/2009 | Auld et al. | 606/15 |
| 2009/0118715 A1 | 5/2009 | Mansour | |
| 2009/0131948 A1 * | 5/2009 | Liu et al. | 606/93 |
| 2009/0131950 A1 * | 5/2009 | Liu | A61B 17/8811 606/94 |
| 2010/0004642 A1 | 1/2010 | Lumpkin | |
| 2010/0076503 A1 * | 3/2010 | Beyar et al. | 606/86 R |
| 2010/0094269 A1 * | 4/2010 | Pellegrino et al. | 606/27 |
| 2010/0204716 A1 * | 8/2010 | Stewart et al. | 606/142 |
| 2011/0112476 A1 * | 5/2011 | Kauphusman et al. | 604/95.04 |
| 2011/0125139 A1 | 5/2011 | Auld et al. | |

OTHER PUBLICATIONS

Mansour Sam, Retinal Probes: Refinining our laser delivery tools, New Retina MD, Winter 2014/2015.*
DORC International, Focus on laserprobes, 2009.*
International Patent Application No. PCT/US2012/059446: International Search Report and Written Opinion dated Jan. 2, 2013, 12 pages.
http://www.prnewswire.com/news-releases/iridex-announces-settlement-of-all-litigation-with-synergetics-57974797.html, Apr. 10, 2007.
http://www.dorc.eu/products.
php?group=18143,18169,18363,18375 &product=113634 &view=product&tab=info, Feb. 16, 2016.

* cited by examiner

PROBES FOR USE IN OPHTHALMIC AND VITREORETINAL SURGERY

TECHNICAL FIELD

The present invention relates generally to ocular surgery devices; and, more particularly, to probes for use in ophthalmic and vitreoretinal surgery. In some embodiments, a fixed curvature laser probe tip is provided that flexes when penetrating a trocar cannula; in other embodiments, a variable curvature laser probe tip is provided that is operable between straight and curved tip configurations.

BACKGROUND

A common treatment often utilized in ophthalmic and vitreoretinal surgery is that of directing laser energy to a surgical site, the targeted surgical site typically being proximate a patient's retina and the surrounding vitreous. Such a surgery is called an endo-ocular photocoagulation procedure, and may be indicated for reattachment of a detached retina, for cauterization of a ruptured blood vessel, for repair of a surgical wound, for removal of defective tissue or vitreous material, and the like.

In order to conduct the endo-ocular photocoagulation procedure, the surgeon must utilize a microsurgical laser probe to deliver the laser energy to the surgical site. The microsurgical laser probe typically comprises a handle with a small cylindrical sleeve, or tip, projecting from the distal end of the handle. An optical fiber element is connected at the proximal end to a laser source, and the fiber is carried through the microsurgical laser probe and into the cylindrical sleeve. The optical fiber element is positioned adjacent the distal end of the cylindrical sleeve in order to effectively deliver laser energy to the intended surgical site.

Prior to beginning the surgery, the surgeon must ascertain and select the appropriate size and type of microsurgical laser probe tip to be used. Currently, microsurgical laser probe tips are available in three predominant sizes: 20 gauge (0.0360 inches), 23 gauge (0.0255 inches), and 25 gauge (0.0205 inches). For smaller gauge probe tips, the use of an appropriately sized trocar cannula is indicated. The trocar cannula is used to pierce the patient's ocular tissue and, thereafter, to provide a passageway for the insertion and support of the probe tip, to prevent the probe tip from bending at the point of entry into the eye, to reduce tearing of the ocular tissue at the insertion point, and to act as a guide channel for the probe tip into the eye. Accordingly, 23 and 25 gauge tips are nearly always used in association with trocar cannulae; whereas, because of relatively larger size and stiffness, 20 gauge tips do not typically require use of trocar cannulae.

When using a 20 gauge probe tip, the surgeon pierces or punctures the ocular tissue in a selected location, inserts the probe tip to the appropriate depth, angle, and position, and begins the endo-ocular photocoagulation procedure. When using either a 23 or 25 gauge probe tip, the surgeon first pierces or punctures the ocular tissue in a selected location with a trocar cannula and positions it on the eye. Thereafter, the 23 or 25 gauge probe tip is passed through the trocar cannula and into the eye to the appropriate depth, angle, and position. Thereafter, the endo-ocular photocoagulation procedure may be conducted.

It is instructive to note that, in order to be most surgically effective, the laser energy should be delivered as nearly perpendicular to the targeted surgical area as possible. Due to positioning of the microsurgical laser probe tip, and the positioning of any associated trocar cannula that may be utilized by the surgeon during the procedure to direct the microsurgical laser probe into the eye, it is most often the case that the surgical site is either inaccessible or located disadvantageously for proper application of laser energy.

In order to solve this problem, curved tips have been introduced for use in association with above-described microsurgical laser probes. Use of such curved tips is advantageous in comparison to use of a straight tip in better orienting the probe tip adjacent the surgical site without need to withdraw and reposition the laser probe, and without the associated secondary punctures of the eye; and, further, in providing for a greater range of coverage inside the eye. Disadvantageously, such curved tips are of fixed curvature and, depending upon the relative diameters of the tip and the associated trocar cannula, sometimes cannot be inserted through straight trocar cannulae. Furthermore, if a different curvature is required in order to properly target the surgical site, the instrument must be withdrawn, and the entire probe must be replaced with one having a tip of appropriate curvature, and the initial wound site re-intruded. Such process is, of course, less than optimal for both patient and surgeon.

To overcome these disadvantages, others have introduced adjustable, directional laser probes that are capable of being adjustably manipulated toward a target surgical site; thereby, seeking to avoid some of the above-referenced disadvantages, while seeking to better direct laser energy to the targeted surgical area. Some such devices are discussed below, and their referenced disclosures are incorporated herein by reference.

U.S. Pat. No. 6,572,608 to Lee et al. provides a probe with a handle and a tubular sleeve. The distal portion of the tubular sleeve has an optical fiber projecting therefrom that can be caused to bend relative to the sleeve by manual manipulation of a mechanism on the probe handle, as the optical fiber is enclosed within a pre-formed curved memory material, such as Nitinol. Disadvantageously, whenever exterior parts of a device move, there is a risk that foreign materials can become lodged within or between those exterior moving parts. Because the Lee et al. design utilizes moving, exterior mechanical parts which move relative to one another within the eye, there is an attendant risk that tissue may become snagged or tangled therebetween. Additionally, when deploying the tip outwardly, the surgeon must carefully ascertain where the tip is located relative to the intended target surgical site in order to prevent puncturing the back of the eye. The surgeon must continually keep a finger positioned on the extension/retraction mechanism to control deployment and retraction of the probe tip, while simultaneously controlling insertion and withdrawal of the probe tip. In other words, the surgeon must undertake a two-step, iterative targeting procedure wherein he/she must withdraw or insert the probe tip, adjust the tip curvature, and repeat until the targeted area can be appropriately accessed. This is a complex, non-intuitive surgical manipulation of the probe instrument, with possible damage resulting to the retina or other ocular tissue.

U.S. Pat. No. 6,984,230 to Scheller et al., a continuation-in-part of U.S. Pat. No. 6,572,608 to Lee et al., further provides that a tubular member carrying the optical fiber may be deployed outwardly from the sleeve.

Disadvantageously, and as with U.S. Pat. No. 6,572,608 to Lee et al., such design utilizes moving, exterior mechanical parts which move relative to one another within the eye, with an attendant risk that tissue may become snagged or tangled therebetween. Additionally, and as with Lee et al., when deploying the tip outwardly, the surgeon must carefully ascertain where the tip is located relative to the intended target surgical site in order to prevent puncturing the back of the eye.

The surgeon must continually keep a finger positioned on the extension/retraction mechanism to control deployment and retraction of the probe tip, while simultaneously controlling insertion and withdrawal of the probe tip. In other words, the surgeon must undertake a two-step, iterative targeting procedure wherein he/she must withdraw or insert the probe tip, adjust the tip curvature, and repeat until the targeted area can be appropriately accessed. This is a complex, non-intuitive surgical manipulation of the probe instrument, with possible damage resulting to the retina or other ocular tissue.

In order to overcome such disadvantages, U.S. Pat. No. 7,766,904 to McGowen, Sr. et al. provides a laser probe capable of functioning in both straight and curved forms. The probe includes an elongated hand piece and rigid cannula affixed thereto to prevent relative translational movement between them. A pre-curved optical fiber inside a memory material, such as Nitinol, extends through the hand piece and cannula, and a slidable button is affixed to the optical fiber through use of a cooperating rigid sleeve. The relative motion of the button with respect to the handle is tied, both visually and physically, to the relative extension, and the resulting curvature, of the optical fiber, with the intended result being avoidance or minimization of damage to the retina or other ocular tissue. Unfortunately, many of the same disadvantages may be seen; to wit, such design utilizes mechanical parts which move relative to one another within the eye, with an attendant risk that tissue may become snagged or tangled therebetween. Further, when deploying the tip outwardly, the surgeon must still guess, or follow additional procedures to ascertain, where the tip is located relative to the intended target surgical site. The surgeon must continually keep a finger positioned on the extension/retraction mechanism to control deployment and retraction of the tip, while simultaneously controlling insertion and withdrawal of the probe tip (the two-step, iterative targeting procedure described above). This results in a complex, non-intuitive surgical manipulation of the instrument, with possible damage resulting to the retina or other ocular tissue.

United States Patent Application 2010/0004642 A1 by Lumpkin proposes a surgical laser probe wherein a hand piece carries an optical fiber through and into a stainless steel tube, the distal end of which carries a length of polyimide bendable tube. The optical fiber is coterminous with the free end of the polyimide tube. A slidable element is installed within a slot in the hand piece and secured to a length of pre-curved Nitinol wire. As the slideable wire element is moved toward the distal end of the hand piece, the Nitinol wire is advanced into the free end of the polyimide tube, increasingly bending the tube and optical fiber away from the longitudinal axis of the stainless steel tube and hand piece. Disadvantageously, this design bends the optical fiber tip about a single point; thus, having a relatively small local radius of curvature, resulting in a relatively large, straight-line offset of the tip. Accordingly, the surgeon may not be able to reach the targeted surgical site due to insufficient curvature of the tip. Furthermore, a small local radius of curvature can, in some cases, reduce or interfere with laser transmission if the radius is below the value recommended by the manufacturer of the optical fiber.

As was discussed above, probe tips having a fixed curvature sometimes cannot be inserted through straight trocar cannulae, depending upon the relative diameters of the tip and the associated trocar cannula. For example, many trocar cannulae are manufactured according to proprietary or customized specifications, such that a trocar cannula manufactured by one company will not be fully compatible with surgical solutions provided by another company. Accordingly, a probe tip providing fixed curvature may be compatible with one model or size of trocar cannula, but not with another. An exemplary solution is proposed in U.S. Pat. No. 7,909,816 to Buzawa, which provides a rigid probe for use with a rigid cannula, the probe having an outside diameter smaller than the inside diameter of the cannula, the probe having one or more sections comprising radii of curvature selected to ensure passage of the probe through the length of the cannula without interference. This is seen to be disadvantageous not only in probe tip manufacture, but also in adding to the complexity of surgical probe entry into and removal from the cannula, and in manipulation and movement of the probe tip during a procedure.

Yet additionally, in most surgeries, one or more additional surgical tool(s), such as a surgical-site illumination instrument, may be needed. Such additional surgical instruments may require additional penetrations into the eye tissue, in which case the recovery time for the patient may be increased, and the risk of complications may likewise be increased.

In an attempt to reduce the need for such additional instruments, particularly those requiring a separate intrusion into the eye, laser energy surgical probes have been designed to deliver both laser energy for treatment and illumination energy, such as for visualization of the targeted surgical site, using a single probe. Thus, only a single penetration into the eye may be required for visualization of the targeted surgical area, as well as for delivery of laser energy to the area to accomplish the surgery.

As such, it is clear that there is an unmet need for an ophthalmic surgical device capable of delivering illumination energy and/or laser energy for treatment of a patient's eye via a single wound site, while maintaining a small diameter probe for reducing unwanted injury to the eye.

Accordingly, what is still needed is an adjustable, directional laser probe for endo-ocular photocoagulation procedures providing, in some embodiments, a fixed curvature laser probe tip that flexes when penetrating a trocar cannula; and in other embodiments, a variable curvature laser probe tip that is operable between straight and curved tip configurations, and that may deliver one or both of laser energy for treatment and illumination energy for visualization of the targeted surgical site, all using a single probe, and all while eliminating or reducing the above-referenced disadvantages in accordance with the detailed disclosure of the inventive subject matter set forth hereinbelow. It is to the provision of such probes that the present invention is directed.

SUMMARY

The present invention is a laser probe for endo-ocular photocoagulation procedures which provides, in some embodiments, a fixed curvature laser probe tip that flexes when penetrating a trocar cannula; and in other embodiments, a variable curvature laser probe tip that is operable between straight and curved tip configurations. In an exemplary embodiment, a hand held fiber optic assembly connects one or more of a light and a laser source via connectors at a proximal end, with the distal, delivery end for use inside the eye when held by a surgeon. The laser energy may be used for endo-ocular photocoagulation procedures involving the retina, surrounding tissue, and vitreous. Illumination energy may, primarily or optionally, be supplied to illuminate the targeted surgical site.

More particularly, in some tip embodiments, an engineered, flexible, plastic tubular material is pre-formed with a section comprising a desired radius of curvature. The curved portion of the tip is sufficiently flexible to straighten sufficiently to pass through a conventional trocar cannula and into the eye, whereafter it resumes its pre-formed, curved shape for use during a surgical procedure.

In other tip embodiments, an engineered, preferably plastic tubular material is pre-formed with a section comprising a desired radius of curvature, and is stiffened internally or externally by use of a preferably stainless steel material. Inside the plastic tubular material is a distal end of an optical fiber, inserted such that its tip is coterminous with the plastic tubular material. A second or other material, such as stainless steel, Nitinol, or the like, surrounds the optical fiber and is free to move along the axis of the assembly, acting to straighten the plastic and optical fiber members as it moves forward via a sliding member, such as a button, that is associated with the hand piece.

Through use of a device according to some embodiments of the present invention, the surgeon has the ability to utilize a fixed-curve probe tip that will pass easily through a straight, conventional trocar cannula, whereafter the original probe tip shape is resumed for the surgical procedure.

Through use of a device according to other embodiments of the present invention, the surgeon has the ability to change the location for energy delivery by changing the angle at the tip by use of a sliding mechanism that acts gradually to straighten a preformed curve at the tip of the probe until a desired angle is achieved. The relative axial movement between the straightening member and the pre-formed curvature at the tip determines the angle of delivery. Advantageously, such a design gives the surgeon the ability to cover a large area compared to a fixed angle tip, while avoiding most of the problems noted in the prior art.

These and other features and advantages of the present invention will become more apparent to those of ordinary skilled in the art after reading the following Detailed Description of Illustrative Embodiments of the invention and the Claims in light of the accompanying drawing Figures.

BRIEF DESCRIPTION OF THE DRAWINGS

Accordingly, the present invention will be understood best through consideration of, and with reference to, the following drawing Figures, viewed in conjunction with the Detailed Description of Illustrative Embodiments of the invention referring thereto, in which like reference numbers throughout the various Figures designate like structure, and in which:

FIG. 5A is partial cut-away side view of another embodiment of a directional tip laser probe for endo-ocular photocoagulation procedures according to the present invention, illustrating the tip thereof in a curved configuration; and, FIG. 5B is a partial cut-away side view of another embodiment of a directional tip laser probe for endo-ocular photocoagulation procedures according to FIG. 5A of the present invention, illustrating the tip thereof in a straight configuration.

It is to be noted that the drawings presented are intended solely for the purpose of illustration and that they are, therefore, neither desired nor intended to limit the invention to any or all of the exact details of construction shown, except insofar as they may be deemed essential to the claimed invention.

DETAILED DESCRIPTION OF ILLUSTRATIVE EMBODIMENTS

In describing preferred embodiments of the present invention illustrated in the figures, specific terminology is employed for the sake of clarity. The invention, however, is not intended to be limited to the specific terminology so selected, and it is to be understood that each specific element includes all technical equivalents that operate in a similar manner to accomplish a similar purpose.

In a form of the present invention chosen for purposes of illustration, exemplary embodiments of which are illustrated in FIGS. 1A, 1B, 1C, and 1D, a flexible tip laser probe for endo-ocular photocoagulation procedures is shown. Hand held fiber optic assembly 10 connects one or more of a light and a laser source S through one or more optical fibers 20 via one or more connector 30 disposed from proximal end 40, with the distal, delivery end 50 of such one or more optical fibers 20 for use inside the eye when held by a surgeon at hand piece 105. The laser energy may be used for endo-ocular photocoagulation procedures involving the retina, surrounding tissue, and vitreous. Illumination energy may be supplied to illuminate the targeted surgical site. Exemplary of such a combined laser and illumination energy delivery device is Applicant's U.S. patent application Ser. No. 11/934,761, filed on Nov. 3, 2007, the disclosure of which is hereby incorporated by reference. In other embodiments, one or more dedicated illumination optical fiber may run parallel to one or more dedicated laser energy optical fiber and connect to respective illumination and laser sources.

In typical embodiments, flexible tip laser probe 10 is provided in 23 and 25 gauge sizes; however, it may also be provided in 20 gauge or other sizes. It is noted that, in accordance with said reference disclosure, flexible tip laser probe 10 for endo-ocular photocoagulation procedures may deliver one or both of laser energy for treatment and illumination energy for visualization of the targeted surgical site.

An engineered, preferably plastic, flexible, tubular material 60 is pre-formed with a radius of curvature C. Tubular material 60 is preferably formed of polyether ether ketone (PEEK), which is an organic polymer thermoplastic material. In the embodiment shown in FIGS. 1A and 1B, tubular material 60 is overlayed by, or inserted into, a rigid portion 70a of hand piece 105. Rigid portion 70a serves to support and stabilize the tip assembly during use. Inside plastic tubular material 60 is disposed a distal end of optical fiber 20, inserted such that its tip is coterminous with the plastic tubular material 60.

Figure 1A:
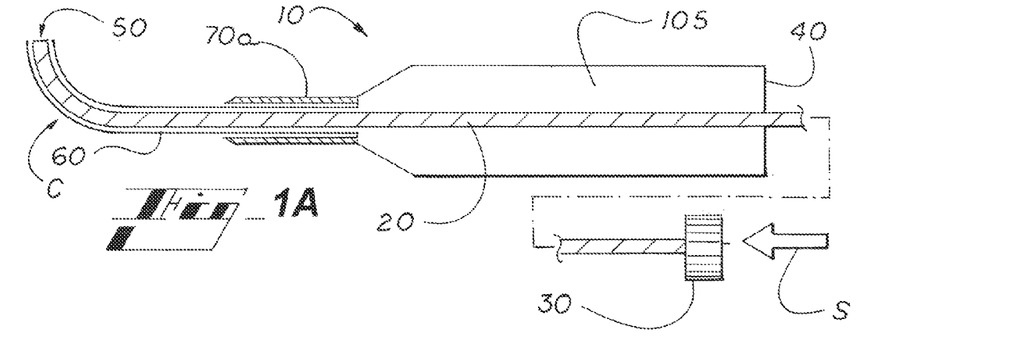
FIG. 1A is a partial cut-away side view of one embodiment of a flexible tip laser probe for endo-ocular photocoagulation procedures according to the present invention.
Figures 1B, 1C:
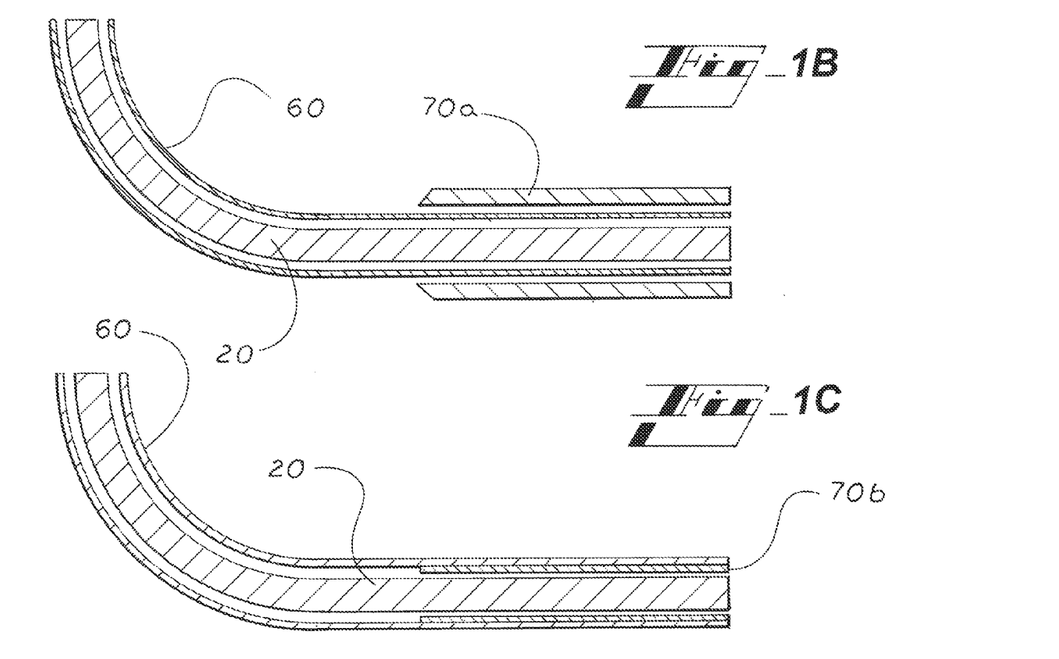
FIG. 1B is an enlarged, partial cut-away side view of an embodiment of a flexible tip laser probe for endo-ocular photocoagulation procedures according to FIG. 1A of the present invention.
FIG. 1C is a partial cut-away side view of another embodiment of a flexible tip laser probe for endo-ocular photocoagulation procedures according to the present invention.

Rigid portion 70a preferably is selected to meet one of the industry-standard outside diameters; to wit, 20, 23, or 25 gauges. So configured, the present invention may be utilized, if desired or required by a surgeon, with a standard size and configuration of trocar cannula. Importantly, as is well-known in the art, larger tip sizes, such as 20 gauge, do not require use of trocar cannulae, but may require suturing of the intrusion site(s). Use of larger tip sizes may also require longer patient healing times. On the other hand, smaller tip sizes, such as 23 or 25 gauge, typically do require use of trocar cannulae, but do not typically require suturing. Use of smaller tip sizes may also shorten patient healing times. Accordingly, it is noted that smaller tip sizes, such as 23 or 25 gauge, are preferred for increasing the rate of a patient's post-surgical recovery, for reducing trauma, and for increasing post-surgical comfort; however, it is contemplated that any appropriate tip size(s) may be utilized.

Specifically, tubular material 60 of the present invention is flexible, rather than rigid, and does not move with respect to hand piece 105. Similarly, optical fiber 20 of the present invention is fixed with respect to hand piece 105 and tubular material 60. This design reduces the potential for puncture or other wounds to retinal or surrounding tissue.

Distinctively, the curved portion of the tip is flexible enough to straighten sufficiently to pass through a conventional trocar cannula and into the eye; whereafter, it resumes its pre-formed, curved shape for use during a surgical procedure. With this design, no special considerations are required of the surgeon with regard to either tip or trocar cannula sizes, other than the conventional surgical choice of compatible tip and trocar cannula size.

FIG. 1C depicts an alternative embodiment of flexible tip laser probe for endo-ocular photocoagulation procedures. All particulars of design, construction, and use, and all other attendant considerations, are as set forth above with regard to the embodiment of FIGS. 1A and 1B, except insofar as will now be discussed. In the embodiment of FIG. 1C, tubular material 60 is underlayed by, or pressed over, a rigid portion 70b of hand piece 105. Rigid portion 70b serves to support and stabilize the tip assembly during use. In this embodiment, tubular material 60 preferably is selected to meet one of the industry-standard outside diameters; to wit, 20, 23, or 25 gauges.

Figure 1D:
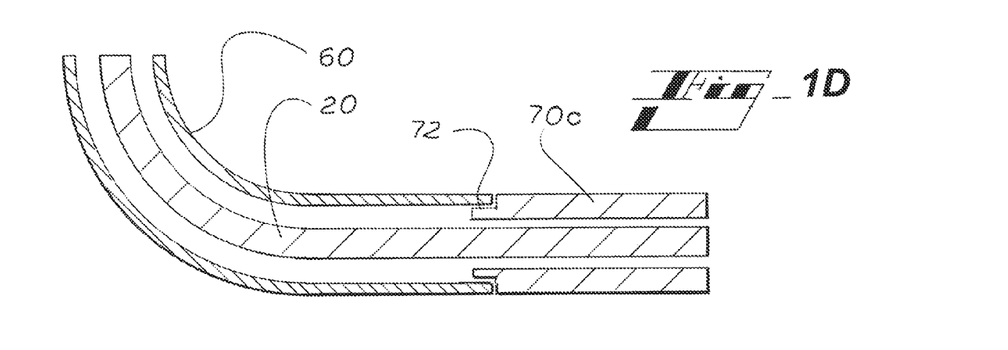
FIG. 1D is a partial cut-away side view of another embodiment of a flexible tip laser probe for endo-ocular photocoagulation procedures according to the present invention.
Figures 2A, 2B:
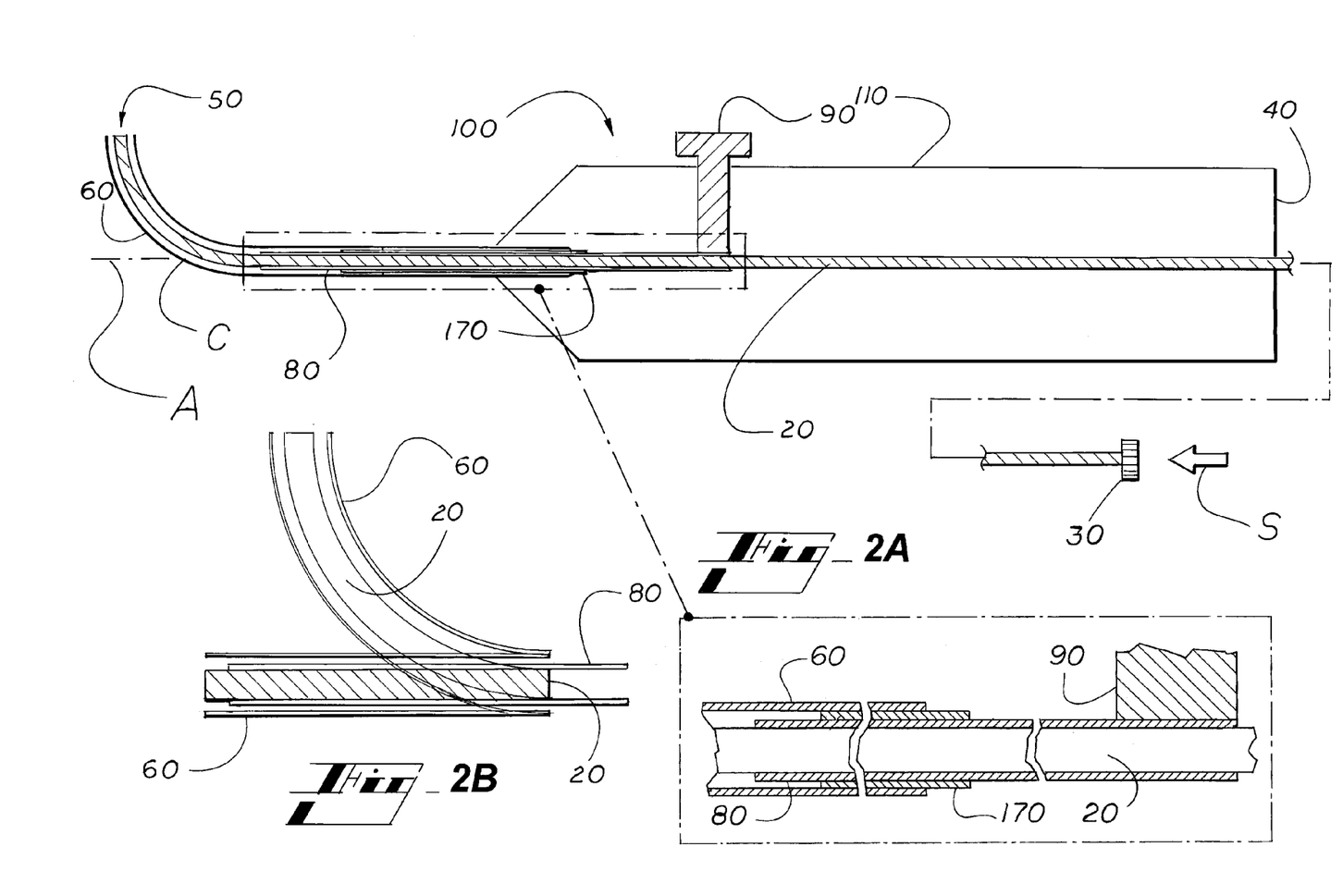
FIG. 2A is a partial cut-away side view of a directional tip laser probe for endo-ocular photocoagulation procedures according to the present invention.
FIG. 2B is a partial cut-away side view of a directional tip laser probe for endo-ocular photocoagulation procedures according to FIG. 2A of the present invention, illustrating movement of the tip thereof between a straight and a curved configuration.
Figure 3A:
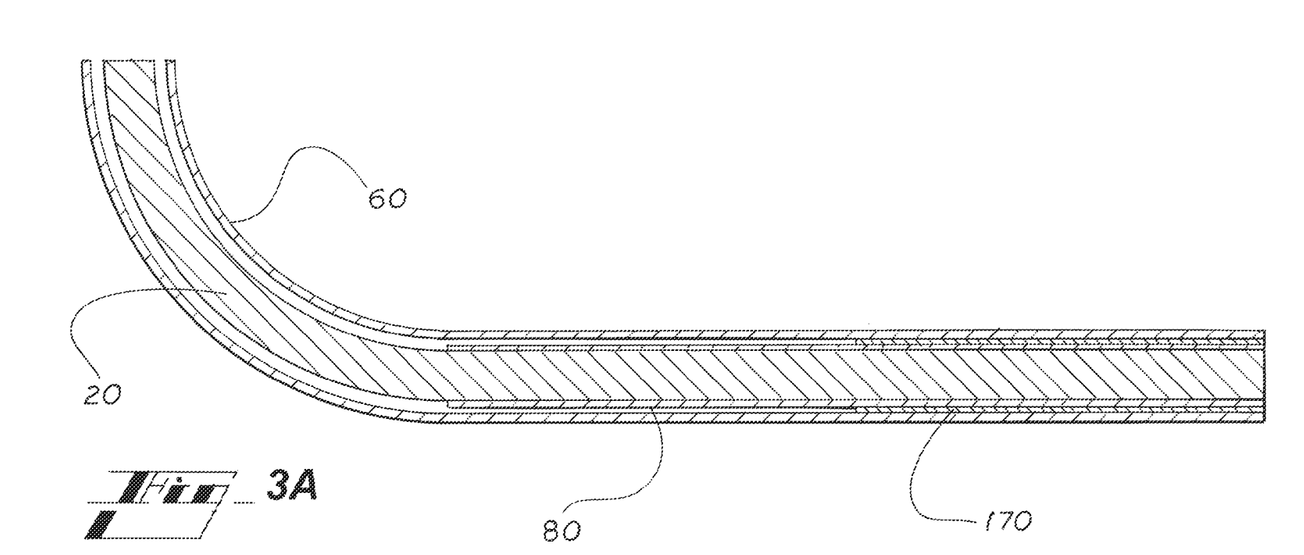
FIG. 3A is partial cut-away side view of one embodiment of a directional tip laser probe for endo-ocular photocoagulation procedures according to FIG. 2A of the present invention, illustrating the tip thereof in a curved configuration.
Figure 3B:
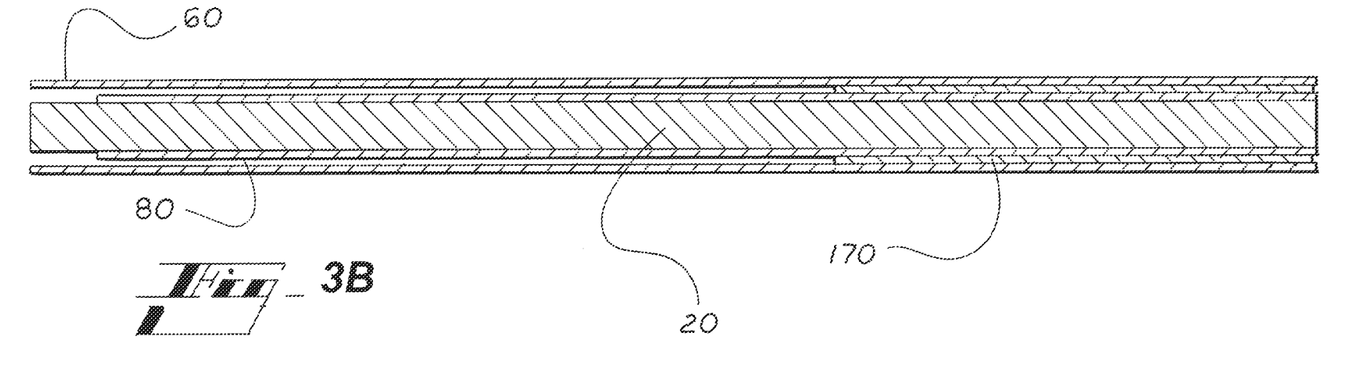
FIG. 3B is a partial cut-away side view of one embodiment of a directional tip laser probe for endo-ocular photocoagulation procedures according to FIG. 2B of the present invention, illustrating the tip thereof in a straight configuration.

FIG. 1D depicts an alternative embodiment of flexible tip laser probe for endo-ocular photocoagulation procedures. All particulars of design, construction, and use, and all other attendant considerations, are as set forth above with regard to the embodiment of FIGS. 1A and 1B, except insofar as will now be discussed. In the embodiment of FIG. 1D, tubular material 60 is underlayed by, or pressed over, a stepped or shouldered end 72 of rigid portion 70c of hand piece 105. Stepped or shouldered end 72 is of reduced outer diameter, disposed to be concentrically joined with plastic tubular material 60. One of ordinary skill in the art will recognize, however, that stepped or shouldered end 72 may, alternatively, be of reduced inside diameter, disposed to be concentrically joined with plastic tubular material 60. Rigid portion 70c serves to support and stabilize the tip assembly during use. In this embodiment, tubular material 60 and rigid portion 70c preferably are selected to meet one of the industry-standard outside diameters; to wit, 20, 23, or 25 gauges.

Other methods and constructions for forming rigid portion 70 are fully contemplated hereby.

Turning now to a form of the present invention chosen for purposes of illustration, exemplary embodiments of which are illustrated in FIGS. 2A, 2B, 3A, and 3B, a directional tip laser probe for endo-ocular photocoagulation procedures is shown. Hand held fiber optic assembly 100 connects one or more of a light and a laser source S through optical fiber 20 via one or more connector 30 disposed from proximal end 40, with the distal, delivery end 50 for use inside the eye when held by a surgeon at hand piece 110. The laser energy may be used for endo-ocular photocoagulation procedures involving the retina, surrounding tissue, and vitreous. Illumination energy may be supplied to illuminate the targeted surgical site, as discussed above with regard to a combined laser and illumination energy delivery device set forth within Applicant's U.S. patent application Ser. No. 11/934,761, filed on Nov. 3, 2007, the disclosure of which has been incorporated by reference. In other embodiments, one or more dedicated illumination optical fiber may run parallel to one or more dedicated laser energy optical fiber and connect to respective illumination and laser sources.

In typical embodiments, flexible tip laser probe 100 is provided in 20, 23, and 25 gauge sizes; however, it may also be provided in other sizes. It is noted that, in accordance with the reference disclosure discussed above, flexible tip laser probe 100 for endo-ocular photocoagulation procedures may deliver one or both of laser energy for treatment and illumination energy for visualization of the targeted surgical site.

An engineered, preferably plastic tubular material 60 is pre-formed with a radius of curvature C, and is stiffened internally in this embodiment, or externally in other embodiments, by use of a preferably stainless steel, Nitinol, or other suitable rigid material, tube 170. Tubular material 60 is preferably formed of polyether ether ketone (PEEK), an organic polymer thermoplastic material described above; however, one of ordinary skill in the art will recognize that a suitable substitute material would be capable of holding a pre-formed curvature, flexing to a straightened form, and then returning approximately to its pre-formed curvature. Accordingly, in some embodiments, Nitinol may serve as an appropriate substitute material. Inside plastic tubular material 60 is disposed a distal end of optical fiber 20, inserted such that its tip is coterminous with the plastic tubular material. Tube 80, formed of a second or other suitable rigid material, such as stainless steel, Nitinol, or the like, surrounds optical fiber 20 and is free to move along longitudinal axis A of the assembly, acting to straighten plastic tubular material 60 and optical fiber 20 as it moves forward, e.g., toward distal, delivery end 50, via sliding member 90, such as a button, that is associated with hand piece 110. It should be apparent that the construction of the device of the present invention should ensure that tube 80 does not pass the tip of optical fiber 20 when tube 80 is fully deployed.

Tubular material 60 preferably is selected to meet one of the industry-standard outside diameters; to wit, 20, 23, or 25 gauges. So configured, the present invention may be utilized, if desired or required by a surgeon, with a standard size and configuration of trocar cannula. Importantly, as is well-known in the art, larger tip sizes, such as 20 gauge, do not require use of trocar cannulae, but may require suturing of the intrusion site(s). Use of larger tip sizes may also require longer patient healing times. On the other hand, smaller tip sizes, such as 23 or 25 gauge, typically do require use of trocar cannulae, but do not typically require suturing. Use of smaller tip sizes may also shorten patient healing times. Accordingly, it is noted that smaller tip sizes, such as 23 or 25 gauge, are preferred for increasing the rate of a patient's post-surgical recovery, for reducing trauma, and for increasing post-surgical comfort; however, it is contemplated that any appropriate tip size(s) may be utilized.

In some embodiments, stainless steel tube 80 may be replaced with a wire of appropriate dimensions and stiffness. In some embodiments, stainless steel tube 80 may be the moving part; or, alternatively, the rest of the assembly could be allowed to move; or, still further alternatively, a combination of both could be effectuated. As will be apparent to one of ordinary skill in the art, what is important is the relative motion interoperably established amongst the defined elements.

It may be observed that, advantageously with the present invention, optical fiber 20 and tubular material 60 do not move with respect to longitudinal axis A, as distinguished from some exemplary prior art devices. By extending and retracting tube 80 via sliding member 90, such as a button, that is associated with hand piece 110, curvature C may be manipulated between a straightened configuration, best seen with reference to FIGS. 2B, 3B, 4B, 5B, or curved configuration, best seen with reference to FIGS. 2A, 3A, 4A, 5A. This allows for intuitive surgical manipulation, as has been described above.

Figures 4A, 4B:
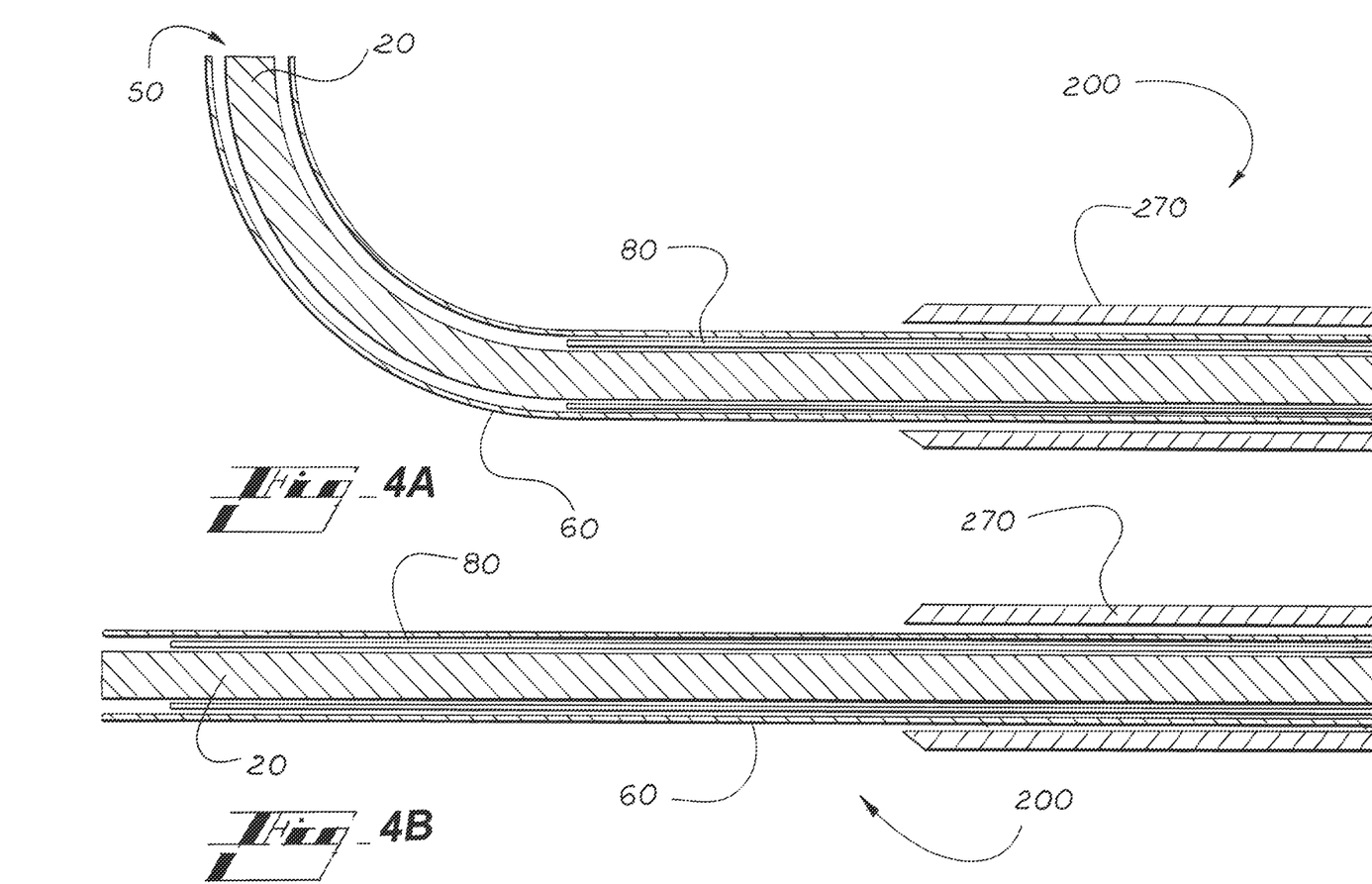
FIG. 4A is partial cut-away side view of another embodiment of a directional tip laser probe for endo-ocular photocoagulation procedures according to the present invention, illustrating the tip thereof in a curved configuration.
FIG. 4B is a partial cut-away side view of another embodiment of a directional tip laser probe for endo-ocular photocoagulation procedures according to FIG. 4A of the present invention, illustrating the tip thereof in a straight configuration.

Turning now to FIGS. 4A and 4B, an alternative embodiment 200 of the present invention is shown. Except as noted, construction of alternative embodiment 200 is equivalent to the embodiment of FIGS. 2A, 2B, 3A, 3B. In alternative embodiment 200, reinforcing tube 270 is provided in order to strengthen and stiffen the construction of distal end 50. In this embodiment, reinforcing tube 270 preferably is selected to meet one of the industry-standard outside diameters; to wit, 20, 23, or 25 gauges. Reinforcing tube 270 is preferably formed of stainless steel or Nitinol and is fit over tubular material 60. As in previous embodiments, FIG. 4A illustrates stainless steel tube 80 fully retracted and tip curved. FIG. 4B illustrates stainless steel tube 80 fully deployed and tip straightened.

Figures 5A, 5B:
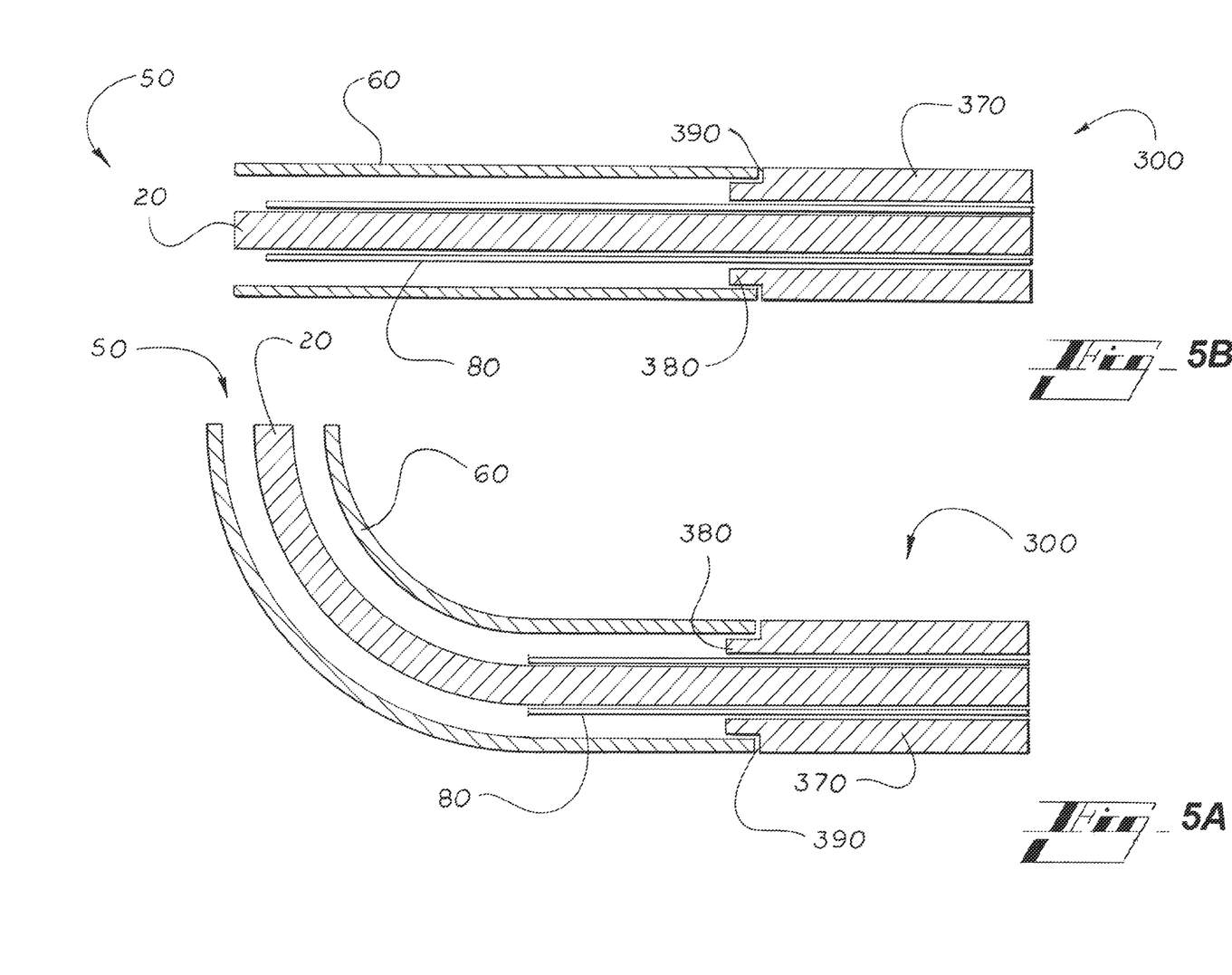

Turning now to FIGS. 5A and 5B, an alternative embodiment 300 of the present invention is shown. Except as noted, construction of alternative embodiment 300 is equivalent to the embodiment of FIGS. 2A, 2B, 3A, 3B. In alternative embodiment 300, reinforcing tube 370 is provided in order to strengthen and stiffen the construction of distal end 50. In this embodiment, reinforcing tube 370 preferably is selected to meet one of the industry-standard outside diameters; to wit, 20, 23, or 25 gauges. Reinforcing tube 370 is preferably formed of stainless steel or Nitinol. In some embodiments, a distal end of reinforcing tube 370 is provided with reduced outer diameter 380, disposed to be concentrically joined with plastic tubular material 60 at joint 390. Other methods and constructions for forming joint 390 are fully contemplated hereby. As in previous embodiments, FIG. 5A illustrates stainless steel tube 80 fully retracted and tip curved. FIG. 5B illustrates stainless steel tube 80 fully deployed and tip straightened.

As should now be apparent, through use of a directional tip laser probe for endo-ocular photocoagulation procedures according to the present invention, the surgeon has the ability to change the location for energy delivery by changing the angle at the tip of the probe by use of a sliding mechanism that acts gradually to straighten a preformed curve at the tip of the probe until a desired angle is achieved. The relative axial movement between the straightening member and the preformed curvature at the tip determines the angle of energy delivery. Advantageously, such a design gives the surgeon the ability to cover a large area compared to a fixed angle tip, while avoiding most of the problems noted in the prior art.

Specifically, tubular material 60 of the present invention is flexible, rather than rigid, and does not move with respect to hand piece 110. Similarly, optical fiber 20 of the present invention is fixed with respect to hand piece 110 and tubular material 60. This design reduces the potential for puncture or other wounds to retinal or surrounding tissue. It should be apparent to one of ordinary skill in the art, however, that the present invention advantageously provides for relative axial movement between the straightening member and the preformed curvature at the tip to determine the angle of delivery. Accordingly, one could provide an embodiment wherein tube 80 is fixed, and wherein optical fiber 20 and tubular material 60 are allowed to move. All such embodiments are fully contemplated hereby.

Further tubular material 60, and by virtue thereof, optical fiber 20 are pre-bent and internally straightened. This design, accordingly, presents no externally moving parts into the eye; thereby, reducing the potential for snagging or tangling of ocular tissue.

Still further, the design of the present invention provides the surgeon with a more intuitive manipulation of the probe than was possible with exemplary prior art devices, such as those of U.S. Pat. Nos. 6,984,230 and/or 7,766,904, as the fiber optic tip is showing all of the time, and there is no guessing where it will deploy. Further the curvature C of the device approximately follows the curvature of the eye.

Even further, the design of the present invention provides better suited and more aggressive angles than exemplary prior art devices, such as that of U.S. Patent Application 2010/0004642, due to the geometry of the device and a more efficient use of space. The present device offers surgeons a truly curved tip, which is advantageous over other designs which bend principally about a single point or which have a relatively small radius of curvature.

In considering other and further alternative embodiments of the present invention, the following observations should become apparent to one of ordinary skill in the art. For example, it should become apparent that the straightening member is not restricted to a tubular construction. Such straightening member could equivalently take the form of a wire, a rod, or the like; however, a tubular construction is preferred for the reason that it offers enhanced stiffness in tight geometries than do the alternatives.

Although tip curvature has been shown in an "upward" configuration, it could be at any angle, dependent upon surgical requirements.

The preferred material for tubular material 60 has been established as PEEK, due to its unique capability to be shaped with heat and to thereafter retain its shape. In alternative embodiments, however, tubular material 60 could be of any material or materials, including layers of materials, that can be straightened by a sliding member on the inside.

Some embodiments of the present invention may include members that are not circular in cross-section, and which may be, for example, oval shapes, elongated shapes, and the like.

Some embodiments of the present invention may include a straightening member that may not, itself, be straight. In such embodiments, the straightening member may be curved in a fashion so that the combined curvature with the tip would achieve a straight tip configuration. This may be the case, for example, where the straightening member must overcome the forces attendant a curvature of the PEEK member.

In some embodiments, the tip of the straightening member may be shaped in a fashion so as to facilitate movement inside the curved PEEK member and not cut into the optical fiber. For example, the end of the straightening member may be disposed at an angle, with the longer portion close to the side of the PEEK material side with the larger radius, and the shorter portion close to the side of the PEEK material with the shorter radius.

Having thus described exemplary embodiments of the present invention, it should be noted by those ordinarily skilled in the art that the within disclosures are exemplary only and that various other alternatives, adaptations, and modifications may be made within the scope and spirit of the present invention. Accordingly, the present invention is not limited to the specific embodiments as illustrated herein, but is only limited by the following claims.

What is claimed:

1. A surgical probe for endo-ocular photocoagulation comprising:
   a. a hand piece;
   b. at least one optical fiber associated with the hand piece for carrying light energy from a light energy source to a distal end of said optical fiber;
   c. a flexible, pre-curved tip comprising a straight portion and a proximal portion, said straight and proximal portions associated with the hand piece at a distal end thereof, said pre-curved tip carrying said distal end of said optical fiber, said pre-curved tip comprising polyether ether ketone (PEEK) material, and wherein said flexible, pre-curved tip has an outer diameter of 20 gauge or less;
   d. a rigid jacket associated with said proximal portion to support and stabilize said flexible, pre-curved tip;
   e. said distal end of said optical fiber being coterminous with a distal end of said pre-curved tip;
   f. a tubular and rigid straightening member operably associated with said hand piece, said optical fiber, and said pre-curved tip, said straightening member at least partially disposed within said straight portion of said pre-curved tip;
   g. said straightening member operable to extend and retract along a longitudinal axis of the surgical probe;
   wherein, in a first mode of operation, said straightening member is configured to extend from within said straight portion of said pre-curved tip and away from the hand piece, acting to straighten said distal ends of said pre-curved tip and said optical fiber as it extends, and wherein, in a second mode of operation, said straightening member is configured to retract into and within said straight portion of said pre-curved tip and toward the hand piece, said pre-curved tip and said optical fiber resuming a curved form.

2. The surgical probe of claim 1, wherein said straightening member is associated with a sliding member that is associated with the hand piece.

3. The surgical probe of claim 2, wherein said sliding member comprises a button.

4. The surgical probe of claim 1, wherein said optical fiber is carried by said hand piece along its longitudinal axis.

5. The surgical probe of claim 1, wherein said straightening member is disposed in association with said optical fiber and within said pre-curved tip.

6. The surgical probe of claim 1, wherein said straightening member comprises stainless steel.

7. The surgical probe of claim 1, wherein said straightening member comprises Nitinol.

8. The surgical probe of claim 1, wherein said probe further carries laser energy to a targeted surgical site.

9. The surgical probe of claim 1, wherein said probe further carries illumination energy to a targeted surgical site.

10. The surgical probe of claim 1 further comprising a laser.

11. The surgical probe of claim 1, operable within a surgical system for endo-ocular photocoagulation, said surgical system further comprising a laser energy source.

12. A probe for ophthalmic and vitreoretinal surgery comprising:
   a. a hand piece;
   b. at least one optical fiber associated with the hand piece for carrying laser energy from a laser energy source to a distal end of said optical fiber;
   c. at least one optical fiber associated with the hand piece for carrying illumination energy from an illumination energy source to a distal end of said optical fiber;
   d. a flexible, pre-curved tip comprising a straight portion and a proximal portion, said straight and proximal portions associated with the hand piece at a distal end thereof, said pre-curved tip carrying said distal ends of said optical fibers, said pre-curved tip comprising polyether ether ketone (PEEK) material, and wherein said flexible, pre-curved tip has an outer diameter of 20 gauge or less;
   e. a rigid jacket associated with said proximal portion to support and stabilize said flexible, pre-curved tip;
   f. said distal ends of said optical fibers being coterminous with a distal end of said pre-curved tip;
   g. a tubular and rigid straightening member operably associated with said hand piece;
   h. said straightening member disposed in association with said optical fibers and within said pre-curved tip;
   i. said straightening member operable to extend and retract along a longitudinal axis of the probe;
   wherein, in a first mode of operation, said straightening member is configured to extend from within said straight portion of said pre-curved tip and away from the hand piece, acting to straighten said distal ends of said pre-curved tip and said optical fibers as it extends, and wherein, in a second mode of operation, said straightening member is configured to retract into and within said straight portion of said pre-curved tip and toward the hand piece, said pre-curved tip and said optical fibers resuming a curved form.

13. The surgical probe of claim 12, wherein said straightening member comprises stainless steel.

14. The surgical probe of claim 12, wherein said straightening member comprises Nitinol.

15. The probe of claim 12 further comprising a laser.

16. A surgical probe for endo-ocular photocoagulation comprising:
   a. a hand piece;
   b. at least one optical fiber associated with the hand piece for carrying light energy from a light energy source to a distal end of said optical fiber;
   c. a flexible, pre-curved tip comprising a straight portion and a proximal portion, said straight and proximal portions associated with the hand piece at a distal end thereof, said pre-curved tip carrying said distal end of said optical fiber, said pre-curved tip comprising a tubular polyether ether ketone (PEEK) material, and wherein said flexible, pre-curved tip has an outer diameter of 20 gauge or less;

d. a rigid jacket associated with said proximal portion to support and stabilize said flexible, pre-curved tip;
e. said distal end of said optical fiber being coterminous with a distal end of said pre-curved tip;
f. a tubular and rigid straightening member operably associated with said hand piece, said optical fiber, and said pre-curved tip, said straightening member at least partially disposed within said straight portion of said pre-curved tip;
g. said straightening member operable to extend and retract along a longitudinal axis of the surgical probe with respect to said pre-curved tip;
wherein, in a first mode of operation, said straightening member is configured to extend from within said straight portion of said pre-curved tip and away from the hand piece, acting to straighten said distal ends of said pre-curved tip and said optical fiber as it extends, and wherein, in a second mode of operation, said straightening member is configured to retract into and within said straight portion of said pre-curved tip and toward the hand piece, said pre-curved tip and said optical fiber resuming a curved form.

17. The surgical probe of claim 16, wherein said straightening member is associated with a sliding member that is associated with the hand piece.

18. The surgical probe of claim 16, wherein said probe further carries laser energy to a targeted surgical site.

19. The surgical probe of claim 16, wherein said straightening member comprises stainless steel.

20. The surgical probe of claim 16, wherein said straightening member comprises Nitinol.

21. The surgical probe of claim 16 further comprising a laser.

22. The surgical probe of claim 16, operable within a surgical system for endo-ocular photocoagulation, said surgical system further comprising a laser energy source.

\* \* \* \* \*